United States Patent [19]

Tokuda et al.

[11] Patent Number: 5,618,555
[45] Date of Patent: Apr. 8, 1997

[54] PERCUTANEOUS ABSORPTION PREPARATION

[75] Inventors: Shoichi Tokuda; Kazuhisa Ninomiya; Yasuhiro Fukushima; Shigeyuki Watanabe, all of Osaka; Mitsuru Ochiai, Saitama; Mutsuo Okumura, Saitama; Yuko Hosokawa, Saitama, all of Japan

[73] Assignees: Itto Denko Corporation, Osaka; Nikken Chemicals Co., Ltd., Tokyo, both of Japan

[21] Appl. No.: 430,384

[22] Filed: Apr. 28, 1995

[30] Foreign Application Priority Data

May 6, 1994 [JP] Japan .................... 6-094241

[51] Int. Cl.$^6$ ........................... A61F 13/00
[52] U.S. Cl. .................. 424/443; 424/448; 424/449; 514/946
[58] Field of Search ............... 424/448, 443, 424/449; 514/946

[56] References Cited

U.S. PATENT DOCUMENTS

| | | | |
|---|---|---|---|
| 4,626,539 | 12/1986 | Aungst et al. | 514/282 |
| 4,806,341 | 2/1989 | Chien | 424/448 |
| 4,844,903 | 7/1989 | Seth | 424/448 |
| 5,026,556 | 6/1991 | Drust | 424/449 |
| 5,069,909 | 12/1991 | Sharma | 424/449 |
| 5,149,538 | 9/1992 | Granger | 424/449 |
| 5,238,933 | 8/1993 | Catz | 514/236.2 |
| 5,240,711 | 8/1993 | Hille et al. | 424/448 |

FOREIGN PATENT DOCUMENTS

| | | |
|---|---|---|
| 0413034 | 2/1991 | European Pat. Off. |
| 8907951 | 9/1989 | WIPO. |
| 9119474 | 12/1991 | WIPO. |
| 9308841 | 5/1993 | WIPO. |

*Primary Examiner*—D. Gabrielle Phelan
*Attorney, Agent, or Firm*—Sughrue, Mion, Zinn, Macpeak & Seas

[57] ABSTRACT

A percutaneous absorption preparation which is excellent in the skin penetration of a non-narcotic analgesic buprenorphine and can sustain a high blood level in a stable state over a long period of time is provided. The percutaneous absorption preparation for administrating buprenorphine hydrochloride and/or buprenorphine, which comprises a support having on one surface thereof a plaster layer containing a pressure-sensitive adhesive, buprenorphine hydrochloride and/or buprenorphine, and a penetration enhancer, wherein the penetration enhancer comprises a combination of a monoglyceride of a fatty acid having 6 to 8 carbon atoms and isopropyl myristate, and the plaster layer contains at least 10% by weight of a monoglyceride off fatty acid having 6 to 8 carbon atoms and at least 5% by weight off isopropyl myristate, with the proviso that the content of the whole penetration enhancer ranges from 25 to 50% by weight. The combined use of the fatty acid monoglyceride and isopropyl myristate as a penetration enhancer synergistically elevates skin penetration of buprenorphine hydrochloride and/or buprenorphine.

7 Claims, No Drawings

PERCUTANEOUS ABSORPTION PREPARATION

FIELD OF THE INVENTION

This invention relates to a percutaneous absorption preparation for percutaneously administering buprenorphine (hydrochloride) which is useful in the relief of the pain in terminal cancer or postoperative pain.

BACKGROUND OF THE INVENTION

According to World Health Organization, the total number of patients with cancer in all the countries in the world amounts to about thirty seven millions. At the final stage of cancer, about 80 to 90% of patients suffer from a pain, though the degree of the pain varies from case to case. In terminal cancer, various social and mental distresses make the physical pain further intolerable. Accordingly, it is highly meaningful not only for the patient himself or herself but also for his or her family members to ease the pain to thereby have a humane time at the end of the life.

The final means for relieving the cancerous pain is the administration of morphine. However there is some hesitation in using morphine since it is a narcotic. Thus it has been required to develop a non-narcotic analgesic with a potent efficacy. Under these circumstances, there have been developed buprenorphine hydrochloride and/or buprenorphine (hereinafter called "buprenorphine (hydrochloride)" in some cases). Buprenorphine (hydrochloride) is a non-narcotic analgesic which has an analgesic efficacy about 30 times higher than that of morphine and is used in the form of injections, sublingual tablets and suppositories in order to relieve cancerous pain and postoperative pain.

However buprenorphine provides no solution to the serious problems accompanying the administration of opium analgesics, e.g., the addictiveness and a low bioavailability (BA) achieved in oral administration. For example, the gastrointestinal BA of buprenorphine is only about 10%, while its sublingual BA is only about 50%. That is to say, buprenorphine should be orally administered in a dose about 10 times more than the dose in the case of intravenous administration, which indicates that the use of buprenorphine suffers from a serious problem. This is because respiratory depression caused by the excessive administration of buprenorphine cannot be treated with an antagonist, e.g., nalorphine which is an antidote suitable for opiate intoxication.

On the other hand, injections should be administered in general by physicians or nurses, which makes domiciliary treatment difficult. Also, injections exhibit only a short duration and thus should be administered at short intervals. These characteristics interfere with the emergent treatment for acute pain. Also, suppositories have a disadvantage of a short duration.

On the other hand, percutaneous administration, which has been vigorously studied recently, has a number of advantages as will be described below. (1) It is expected that the percutaneous administration achieves a drug effect lasting for 24 hours or longer, which makes such frequent administration unnecessary as required in the cases of injections, sublingual tablets and suppositories. (2) It is expected that the percutaneous administration makes absorption uniform and thus excessive administration can be avoided. Therefore side effects can be relieved. (3) The percutaneous administration causes neither any unevenness in the absorption/retention in the digestive tracts nor first pass effect in the liver. (4) The percutaneous administration is applicable even to a patient for whom oral administration is impossible.

However, drugs are generally poor in percutaneous absorption and thus can be hardly absorbed in a required dose at a practically available adhesion area, i.e., 100 cm$^2$ or less. This is seemingly because the horny layer of the skin serves as a barrier. Buprenorphine (hydrochloride) is not an exception but shows extremely poor percutaneous absorption. Therefore attempts have been made to develop a percutaneous absorption preparation of buprenorphine (hydrochloride) which has many advantages as described above (for example, JP-A-2-191214, JP-A-2-191215, JP-A-2-237915, JP-A-3-163014, JP-A-3-193732, JP-A-4-217926, U.S. Pat. No. 5,069,909; the term "JP-A" as used herein means an "unexamined published Japanese patent application"). However most of these patents are not usable in practice, since the skin penetration of a drug is discussed in the form of a solution or a penetration enhancer is merely added to a pressure-sensitive adhesive without any special idea and thus a percutaneous absorption preparation can be hardly formed thereby. In addition, penetration enhancers comprising organic acids, which might induce skin irritation, are employed in some of these patents. Thus they involve some problems from the viewpoint of safety.

When a percutaneous penetration enhancer is added in order to improve the percutaneous absorption of buprenorphine (hydrochloride), the penetration enhancer sometimes oozes out to the surface of a plaster thus changing the properties of the preparation. Further, the addition of a plasticizer or a penetration enhancer to the pressure-sensitive adhesive causes a decrease in the cohesive force and, as a result, the pressure-sensitive adhesive remains on the skin surface. To solve this problem, attempts have been made to add silicic acid anhydride (hydrophilic silicic anhydride, hydrophobic silicic anhydride) to thereby enhance the cohesive force (JP-A-3-291218, JP-A-4-299927, JP-A-4-312525). However the addition of silicic anhydride results in a problem that the thixotropic properties of the plaster solution thus elevated interfere with application.

The present invention, which has been completed in order to solve the above-mentioned problems, aims at providing a percutaneous absorption preparation with excellent skin penetration of buprenorphine (hydrochloride). The present invention also aims at providing a percutaneous absorption preparation having excellent skin penetration of buprenorphine (hydrochloride) and an excellent storage stability.

The present inventors have conducted extensive studies in order to solve the above-mentioned problems. As a result, they have found out that the skin penetration of buprenorphine (hydrochloride) can be synergistically elevated by using a combination of a monoglyceride of a fatty acid having 6 to 8 carbon atoms and isopropyl myristate as a penetration enhancer, thus completing the present invention.

SUMMARY OF THE INVENTION

The present invention provides a percutaneous absorption preparation for administrating buprenorphine hydrochloride and/or buprenorphine, which comprises a support having on one surface thereof a plaster layer containing a pressure-sensitive adhesive, buprenorphine hydrochloride and/or buprenorphine, and a penetration enhancer, wherein the penetration enhancer comprises a combination of a monoglyceride of a fatty acid having 6 to 8 carbon atoms and isopropyl myristate, and the plaster layer contains at least 10% by weight of a monoglyceride of fatty acid having 6 to 8 carbon atoms and at least 5% by weight of isopropyl myristate, with the proviso that the content of the whole penetration enhancer ranges from 25 to 50% by weight. The position of the fatty acid group in the monoglyceride is arbitrary.

Although either the monoglyceride of fatty acid having 6 to 8 carbon atoms or isopropyl myristate to be used as the penetration enhancer for buprenorphine (hydrochloride) in the present invention cannot impart the desired skin penetration when employed alone, the combined use of these substances can achieve a synergistic effect of enhancing the skin penetration.

When the percutaneous absorption preparation is stored at a high temperature, the percutaneous penetration enhancer, which is contained in the preparation in an amount of from 25 to 50% by weight, is liable to ooze out onto the surface of the plaster. When the penetration enhancer oozes out onto the surface of the plaster, there arises a problem that the release of the drug from the preparation is promoted. The present inventors have concentrated their attention on discussing this point and consequently found out that the oozing-out of the penetration enhancer can be prevented and thus the change in the release of the drug can be suppressed by adding hydrated silicic acid to the plaster. Although the difference between hydrated silicic acid and silicic anhydride resides simply in the presence or absence of water of crystallization, the properties achieved by adding these compounds to the preparation of the present invention largely differ from each other. That is to say, the addition of silicic anhydride causes a disadvantageous phenomenon, i.e., a decrease in the release of the drug from the preparation with the passage of time, while the addition of hydrated silicic acid induces no change with the passage of time. There is an additional difference. Namely, the use of silicic anhydride makes the application difficult because of the thixotropic properties, while the use of hydrated silicic acid makes the application easy and thus facilitates the formation of the plaster layer.

DETAILED DESCRIPTION OF THE INVENTION

Now, the percutaneous absorption preparation according to the present invention will be described in detail.

The support to be used in the present invention may be made of an arbitrary material, so long as buprenorphine (hydrochloride) and the penetration enhancer contained in the plaster layer cannot permeate therethrough. The support serves as a protector for the plaster layer and, at the same time, as a supporting base. Examples of materials suitable for the formation of the support include polyethylene terephthalate, polypropylene and metallic foils. These materials may be used in the form of either a single-layer film or a multi-layer film formed by laminating a number of layers. Also, use can be made of a multi-layer film formed by laminating a woven fabric or a non-woven fabric made of such a material onto a film made of such a material. It is also possible to use a multi-layer film formed by laminating a material, through which the drug or the penetration enhancer can penetrate, onto a film made of the above-mentioned non-permeable material. Although the thickness of the support is not particularly restricted so long as the above-mentioned functions can be established, it is suitable from the viewpoint of handling properties that the thickness falls within a range of from 2 to 100 μm.

Preferable examples of the monoglyceride of fatty acid having 6 to 8 carbon atoms to be used in the present invention include caproic acid monoglyceride and caprylic acid monoglyceride. For example, a commercially available product "Sunsoft 700P-2" (manufactured by Taiyo Kagaku Co., Ltd.) can be used as such. It is not suitable to use fatty acid diglycerides or triglycerides, since these substances prevent the absorption of buprenorphine (hydrochloride). When used alone, isopropyl myristate scarcely promotes the percutaneous absorption of buprenorphine (hydrochloride). However, the combined use of isopropyl myristate with a monoglyceride of fatty acid having 6 to 8 carbon atoms achieves a synergistic effect of promoting the absorption. As the isopropyl myristate, a commercially available product "IPM-100" (produced by Nikko Chemicals Co., Ltd.) can be used as such.

In the present invention, a combination of a monoglyceride of fatty acid having 6 to 8 carbon atoms with isopropyl myristate is used as a penetration enhancer. The plaster layer of the preparation according to the present invention contains as a penetration enhancer at least 10% by weight of the monoglyceride of fatty acid having 6 to 8 carbon atoms and at least 5% by weight of isopropyl myristate, and the content of the whole penetration enhancer (i.e., the total amount of the fatty acid monoglyceride and isopropyl myristate) in the plaster ranges from 25 to 50% by weight. It is preferred that the ratio by weight of the fatty acid monoglyceride to isopropyl myristate to be contained in the plaster layer is 10:1 to 2:3, more preferably 7:1 to 1:1.

The effect of promoting the absorption is synergistically enhanced by using at least 1% by weight of a monoglyceride of fatty acid having 6 to 8 carbon atoms together with isopropyl myristate. When the amount of the monoglyceride of fatty acid having 6 to 8 carbon atoms is smaller than 10% by weight, however, it is impossible to obtain such an effect of promoting the absorption to achieve the desired analgesic effect at a practical adhesion area (i.e., 100 cm$^2$ or less), even though isopropyl myristate is used together. When the amount of the isopropyl myristate is smaller than 5% by weight, on the other hand, it is impossible to obtain such an effect of promoting the absorption to achieve the desired analgesic effect at a practical adhesion area (i.e., 100 cm$^2$ or less), even though the monoglyceride of fatty acid having 6 to 8 carbon atoms is used together. Also, when the content of the whole penetration enhancer is smaller than 25% by weight, the percutaneous absorption of the desired amount of buprenorphine (hydrochloride) cannot be achieved at a practical adhesion area (i.e., 100 cm$^2$ or less). When the content of the whole penetration enhancer exceeds 50% by weight, on the other hand, the plaster is softened and undergoes stringiness (cohesive failure), even though crosslinking is induced by adding a crosslinking agent thereto. In this case, it is difficult to retain the shape of the preparation and a residue sometimes remains on the skin after peeling off the preparation. Regarding the amount of the penetration enhancer, it is therefore preferable to use at least 15% by weight of the fatty acid monoglyceride and at least 10% by weight of isopropyl myristate.

In the present invention, buprenorphine hydrochloride and/or buprenorphine are used as a drug. The drug is used in a proportion of from 2.5 to 20% by weight, preferably from 5 to 10% by weight in the plaster. Although the skin penetration of the drug is enhanced with an increase in the drug concentration, when the drug concentration exceeds 10% by weight, the ratio of the amount the drug permeating through the skin to the amount of the drug contained in the preparation is lowered. At a drug concentration exceeding 20% by weight, this tendency becomes very apparent, which is undesirable from the viewpoint of the effective utilization of the drug. When the drug concentration is smaller than 2.5% by weight, on the other hand, an excessively large adhesion area of the preparation is required in order to attain the drug concentration in the blood (blood level) for expressing a sufficient drug effect. It is preferable that the adhesion area is not more than 100 cm$^2$. It is also preferable that the adhesion area is not less than 5 cm$^2$, since an excessively small adhesion area makes the application difficult.

The percutaneous absorption preparation of the present invention can contain hydrated silicic acid in the plaster so as to prevent the penetration enhancer from oozing out onto the surface of the plaster during storage. The hydrated silicic acid to be used in the present invention is generally represented by the general formula $SiO_2 \cdot nH_2O$ and called hydrated amorphous silicon oxide or hydrated silicon dioxide. For example, a commercially available product "Carplex" (manufactured by Shionogi & Co., Ltd.) may be used therefor as such. The hydrated silicic acid is used in an amount of from 2.5 to 20% by weight, preferably from 5 to 15% by weight, in the plaster. When the amount of hydrated silicic acid is smaller than 2.5% by weight, hydrated silicic acid can achieve only an insufficient effect of suppressing the oozing out of the penetration enhancer. When it exceeds 20% by weight, on the other hand, the effect of suppressing the oozing out of the penetration enhancer cannot be improved any more but the adhesive property is deteriorated. Further, hydrated silicic acid is effective in relieving the stringiness (cohesive failure). The skin penetration rate of a preparation containing hydrated silicic acid is almost the same as that of a preparation free from hydrated silicic acid. Thus it is proved that hydrated silicic acid has no effect of promoting percutaneous absorption.

As the pressure-sensitive adhesive to be used in the present invention, it is preferable to select an acrylic pressure-sensitive adhesive which is a copolymer of acrylic acid with an acrylic monomer copolymerizable therewith and shows a pressure-sensitive adhesive property at ordinary temperatures. The copolymer of acrylic acid with an acrylic monomer copolymerizable therewith preferably comprises the former monomer and the latter monomer in a weight ratio of 2:98 to 10:90 and preferably has a number-average molecular weight of 30,000 to 100,000. It is particularly suitable to use a copolymer of acrylic acid with an alkyl acrylate. From the viewpoints of the easiness in the crosslinking, the appropriate adhesive property and the internal cohesive force of the pressure-sensitive adhesive, it is preferable to use a copolymer of acrylic acid with an alkyl acrylate having 4 to 15 carbon atoms in the alkyl group. This pressure-sensitive adhesive is advantageous to easily perform crosslinking, if necessary.

Specific examples of the alkyl acrylate include those having linear alkyl groups such as butyl, pentyl, hexyl, heptyl, octyl, nonyl, decyl, undecyl, dodecyl and tridecyl groups and branched alkyl groups such as 2-ethylhexyl group. Either one of these alkyl acrylates or a mixture thereof may be used.

The plaster in the percutaneous absorption preparation of the present invention may be subjected to crosslinking to thereby give a crosslinked pressure-sensitive adhesive for preventing stringiness (cohesive failure). The occurrence of stringiness is not preferable from a practical viewpoint, since some portion of the plaster remains on the releasing sheet after the preparation is peeled off from the releasing sheet or a residue sometimes remains on the skin after peeling off the preparation which has been applied thereto. It is therefore preferable to effect a crosslinking treatment to thereby enhance the cohesive force and prevent the stringiness. For the crosslinking treatment, chemical crosslinking may be performed with the use of a crosslinking agent such as a polyisocyanate compound, an organic peroxide, an organic metal salt, a metal alcoholate or a metal chelate compound. In the present invention, it is preferable to select a trifunctional isocyanate or a metal alcoholate or a metal chelate compound comprising titanium or aluminum, from among those cited above, as the crosslinking agent because of the reactivity and easiness in handling. Examples thereof include trimethylolpropane adduct of hexamethylene diisocyanate (Coronate HL manufactured by Nippon Polyurethane Industry Co., Ltd.), trimethylolpropane adduct of xylylene diisocyanate (Coronate L; manufactured by Nippon Polyurethane Industry Co., Ltd.), tetraoctylene glycol titanium (Tyzer OG; manufactured by du Pont), aluminum diisopropoxide monoethylacetate (ALCH; manufactured by Kawaken Fine Chemicals Co., Ltd.) and aluminum tris(ethylacetoacetate) (ALCH-TR; manufactured by Kawaken Fine Chemicals Co., Ltd.). Such a crosslinking agent may be used in an amount of approximately from 0.01 to 2 parts by weight per 100 parts by weight of the pressure-sensitive adhesive.

As described above, hydrated silicic acid is effective in suppressing stringiness. Therefore, a preparation containing hydrated silicic acid may be optionally subjected to crosslinking.

The percutaneous absorption preparation according to the present invention is usually provided with a releasing liner in order to prevent the release of buprenorphine (hydrochloride) and the penetration enhancer before the application and to protect the adhesive surface of the plaster layer. The releasing liner is one made of an appropriate material, through which buprenorphine (hydrochloride) and the penetration enhancer contained in the plaster layer cannot permeate, and having at least one surface which has been subjected to releasing treatment, e.g., with silicone. Examples of materials preferable therefor include polyethylene terephthalate and polypropylene.

The thickness of the plaster layer preferably ranges from 10 to 200 µm, still preferably from 20 to 100 µm, though the present invention is not restricted thereto. An excessively thin plaster layer requires an enlarged adhesion area of the preparation in order to achieve the analgesic effect. On the other hand, an excessively thick plaster layer causes a decrease in the utilization ratio of the drug (i.e., the ratio of the amount the drug permeating through the skin to the amount of the drug contained in the preparation), which is inefficient.

The percutaneous absorption preparation according to the present invention can be prepared by, for example, the following method.

Under an inert gas atmosphere, monomer(s) for forming a pressure-sensitive adhesive are reacted with a polymerization initiator in an appropriate organic solvent (for example, ethyl acetate) to thereby give a solution of the pressure-sensitive adhesive. Buprenorphine hydrochloride and/or buprenorphine and a penetration enhancer are dissolved (or dispersed) in an appropriate organic solvent and the above-mentioned pressure-sensitive adhesive solution is added thereto optionally together with a crosslinking agent. Thus a pressure-sensitive adhesive solution for forming a plaster layer is obtained. To produce a preparation containing hydrated silicic acid, hydrated silicic acid may be added to this pressure-sensitive adhesive solution.

Next, the above-mentioned pressure-sensitive adhesive solution is applied onto the surface of a releasing liner which has been subjected to releasing treatment, in such a manner as to form a plaster layer of a desired thickness and, after eliminating the solvent, adhered to a support. Alternatively, the above-mentioned pressure-sensitive adhesive solution is applied onto a support in such a manner as to form a plaster layer of a desired thickness and, after eliminating the solvent, adhered to the surface of a releasing liner which has been subjected to releasing treatment. Thus the percutaneous absorption preparation can be obtained. The pressure-sensitive adhesive solution may be applied by a method commonly employed in the art, for example, casting, roll coating, reverse coating, doctor blade coating or bar coating.

The percutaneous absorption preparation of the present invention may be subjected to crosslinking at an appropriate stage if necessary. For example, chemical crosslinking may be performed by heating the preparation formed in the above-mentioned manner to about 40 to about 70° C. for 24 to 96 hours. Alternatively, the pressure-sensitive adhesive composition is subjected to crosslinking before the formation of the plaster layer and then stirred for dispersion by an appropriate means (for example, using a mixer). Then a plaster layer is formed by the same procedure as the one described above to thereby give a percutaneous absorption preparation.

The effect of the percutaneous absorption preparation of the present invention is expressed by adhering the plaster layer formed on one surface of the support to the skin and thus allowing the skin to absorb the drug. When the plaster layer has only an insufficient adhesive property to the skin at the step of application, the preparation may be fixed onto the skin by using other means. Although the means for fixing is not particularly restricted, it is convenient to fix the preparation onto the skin with the use of an adhesive sheet, etc.

To further illustrate the present invention in greater detail, and not by way of limitation, the following Examples will be given. In the following Examples, all parts and % are by weight.

EXAMPLE 1

Under an inert gas atmosphere, 5 parts of acrylic acid and 95 parts of 2-ethylhexyl acrylate were fed into a flask and 0.3 parts of azobisisobutyronitrile was added thereto as a polymerization initiator. Then these monomers were polymerized in ethyl acetate while maintaining the temperature at 60° C. Thus an acrylic pressure-sensitive adhesive solution (solid content: 40%) was obtained.

To 5 parts of buprenorphine hydrochloride were added 10 parts of caprylic acid monoglyceride, 15 parts of isopropyl myristate and 196 parts of ethyl acetate. Then, buprenorphine hydrochloride was dispersed by thoroughly stirring. To the resulting dispersion were added 174.5 parts (69.8 parts in terms of solid matters) of the pressure-sensitive adhesive solution described above and 0.2 parts of trimethylolpropane adduct of hexamethylene diisocyanate. After stirring well, a viscous solution was obtained, which is sometimes referred to as "a plaster solution".

This viscous solution was applied onto a polyester releasing liner of 75 μm in thickness in such a manner as to give a dry thickness of 60 μm and dried at 90° C. for 4 minutes. Next, a polyethylene terephthalate support of 12 μm in thickness was adhered thereto. Thus a percutaneous absorption preparation according to the present invention was obtained.

COMPARATIVE EXAMPLE 1

By using the pressure-sensitive adhesive solution obtained in the above Example 1, a plaster solution was prepared in such a manner as to give the composition as specified below after drying. Then the procedure of Example 1 was repeated to thereby give a percutaneous absorption preparation. This plaster solution contained no isopropyl myristate.

| | |
|---|---|
| Buprenorphine hydrochloride | 5 parts. |
| Caprylic acid monoglyceride | 10 parts. |
| Pressure-sensitive adhesive (in terms of solid matters) | 84.8 parts. |
| Trimethylolpropane adduct of hexamethylene diisocyanate | 0.2 parts. |

COMPARATIVE EXAMPLE 2

By using the pressure-sensitive adhesive solution obtained in the above Example 1, a plaster solution was prepared in such a manner as to give the composition as specified below after drying. Then the procedure of Example 1 was repeated to thereby give a percutaneous absorption preparation. This plaster Solution contained 15 parts of the penetration enhancer in total.

| | |
|---|---|
| Buprenorphine hydrochloride | 5 parts. |
| Caprylic acid monoglyceride | 10 parts. |
| Isopropyl myristate | 5 parts. |
| Pressure-sensitive adhesive (in terms of solid matters) | 79.8 parts. |
| Trimethylolpropane adduct of hexamethylene diisocyanate | 0.2 parts. |

EXAMPLE 2

To 5 parts of buprenorphine hydrochloride were added 20 parts of caprylic acid monoglyceride, 10 parts of isopropyl myristate and 203 parts of ethyl acetate. Then, buprenorphine hydrochloride was dispersed by thoroughly stirring. To the resulting dispersion were added 162.0 parts (64.8 parts in terms of solid matters) of the pressure-sensitive adhesive solution obtained in Example 1 and 0.2 parts of trimethylolpropane adduct of hexamethylene diisocyanate. After stirring well, a viscous solution was obtained.

Then the procedure of Example 1 was repeated to thereby give a percutaneous absorption preparation of the present invention having a thickness of 60 μm.

To 5 parts of buprenorphine hydrochloride were added 20 parts of caprylic acid monoglyceride, 20 parts of isopropyl myristate and 181 parts of ethyl acetate. Then, buprenorphine hydrochloride was dispersed by thoroughly stirring. To the resulting dispersion were added 137.0 parts (54.8 parts in terms of solid matters) of the pressure-sensitive adhesive solution obtained in Example 1 and 0.2 parts of trimethylolpropane adduct of hexamethylene diisocyanate. After stirring well, a viscous solution was obtained.

Then the procedure of Example 1 was repeated to thereby give a percutaneous absorption preparation of the present invention having a thickness of 60 μm.

EXAMPLE 4

To 5 parts of buprenorphine hydrochloride were added 30 parts of caprylic acid monoglyceride, 10 parts of isopropyl myristate and 181 parts of ethyl acetate. Then, buprenorphine hydrochloride was dispersed by thoroughly stirring. To the resulting dispersion were added 137.0 parts (54.8 parts in terms of solid matters) of the pressure-sensitive adhesive solution obtained in Example 1 and 0.2 parts of trimethylolpropane adduct of hexamethylene diisocyanate. After stirring well, a viscous solution was obtained.

Then the procedure of Example 1 was repeated to thereby give a percutaneous absorption preparation of the present invention having a thickness of 60 μm.

EXAMPLE 5

By using the pressure-sensitive adhesive solution obtained in the above Example 1, a plaster solution was prepared in such a manner as to give the composition as specified below after drying. Then the procedure of Example 4 was repeated to thereby give a percutaneous absorption preparation. This plaster solution contained no trimethylpropane adduct of hexamethylene diisocyanate.

| | |
|---|---|
| Buprenorphine hydrochloride | 5 parts. |
| Caprylic acid monoglyceride | 30 parts. |
| Isopropyl myristate | 10 parts. |
| Pressure-sensitive adhesive (in terms of solid matters) | 55 parts. |

COMPARATIVE EXAMPLE 3

By using the pressure-sensitive adhesive solution obtained in the above Example 1, a plaster solution was prepared in such a manner as to give the composition as specified below after drying. Then the procedure of Example 4 was repeated to thereby give a percutaneous absorption preparation. This plaster solution contained no caprylic acid monoglyceride.

| | |
|---|---|
| Buprenorphine hydrochloride | 5 parts. |
| Isopropyl myristate | 10 parts. |
| Pressure-sensitive adhesive (in terms of solid matters) | 84.8 parts. |
| Trimethylolpropane adduct of hexamethylene diisocyanate | 0.2 parts. |

COMPARATIVE EXAMPLE 4

By using the pressure-sensitive adhesive solution obtained in the above Example 1, a plaster solution was prepared in such a manner as to give the composition as specified below after drying. Then the procedure of Example 4 was repeated to thereby give a percutaneous absorption preparation. This plaster solution contained no isopropyl myristate.

| | |
|---|---|
| Buprenorphine hydrochloride | 5 parts. |
| Caprylic acid monoglyceride | 30 parts. |
| Pressure-sensitive adhesive (in terms of solid matters) | 64.8 parts. |
| Trimethylolpropane adduct of hexamethylene diisocyanate | 0.2 parts. |

COMPARATIVE EXAMPLE 5

By using the pressure-sensitive adhesive solution obtained in the above Example 1, a plaster solution was prepared in such a manner as to give the composition as specified below after drying. Then the procedure of Example 4 was repeated to thereby give a percutaneous absorption preparation. This plaster solution contained neither caprylic acid monoglyceride nor isopropyl myristate.

| | |
|---|---|
| Buprenorphine hydrochloride | 5 parts. |
| Pressure-sensitive adhesive (in terms of solid matters) | 94.8 parts. |
| Trimethylolpropane adduct of hexamethylene diisocyanate | 0.2 parts. |

COMPARATIVE EXAMPLE 6

By using the pressure-sensitive adhesive solution obtained in the above Example 1, a plaster solution was prepared in such a manner as to give the composition as specified below after drying. Then the procedure of Example 4 was repeated to thereby give a percutaneous absorption preparation. This plaster solution contained neither caprylic acid monoglyceride, isopropyl myristate nor trimethylolpropane adduct of hexamethylene diisocyanate.

| | |
|---|---|
| Buprenorphine hydrochloride | 5 parts. |
| Pressure-sensitive adhesive (in terms of solid matters) | 95 parts. |

EXAMPLE 6

To 10 parts of buprenorphine hydrochloride were added 35 parts of caprylic acid monoglyceride, 15 parts of isopropyl myristate and 173 parts of ethyl acetate. Then, buprenorphine hydrochloride was dispersed by thoroughly stirring. To the resulting dispersion were added 99.25 parts (39.7 parts in terms of solid matters) of the pressure-sensitive adhesive solution obtained in Example 1 and 0.3 parts of trimethylolpropane adduct of hexamethylene diisocyanate. After stirring well, a viscous solution was obtained.

Then the procedure of Example 1 was repeated to thereby give a percutaneous absorption preparation of the present invention having a thickness of 40 μm.

COMPARATIVE EXAMPLE 7

By using the pressure-sensitive adhesive solution obtained in the above Example 1, a plaster solution was prepared in such a manner as to give the composition as specified below after drying. Then the procedure of Example 6 was repeated to thereby give a percutaneous absorption preparation. This plaster solution contained neither caprylic acid monoglyceride nor isopropyl myristate.

| | |
|---|---|
| Buprenorphine hydrochloride | 10 parts. |
| Pressure-sensitive adhesive (in terms of solid matters) | 89.7 parts. |
| Trimethylolpropane adduct of hexamethylene diisocyanate | 0.3 parts. |

EXAMPLE 7

To 10 parts of buprenorphine hydrochloride were added 45 parts of caprylic acid monoglyceride, 5 parts of isopropyl myristate and 173 parts of ethyl acetate. Then, buprenorphine hydrochloride was dispersed by thoroughly stirring. To the resulting dispersion were added 99.25 parts (39.7 parts in terms of solid matters) of the pressure-sensitive adhesive solution obtained in Example 1 and 0.3 parts of trimethylolpropane adduct of xylylene diisocyanate. After stirring well, a viscous solution was obtained.

This viscous solution was applied onto a polyester releasing liner of 75 μm in thickness in such a manner as to give a dry thickness of 20 μm and dried at 90° C. for 4 minutes. Next, a polypropylene support of 12 μm in thickness was adhered thereto. Thus a percutaneous absorption preparation according to the present invention was obtained.

COMPARATIVE EXAMPLE 8

By using the pressure-sensitive adhesive solution obtained in the above Example 1, a plaster solution was prepared in such a manner as to give the composition as specified below after drying. Then the procedure of Example 7 was repeated to thereby give a percutaneous absorption preparation. This plaster solution contained no caprylic acid monoglyceride.

| | |
|---|---|
| Buprenorphine hydrochloride | 10 parts. |
| Isopropyl myristate | 5 parts. |
| Pressure-sensitive adhesive (in terms of solid matters) | 84.7 parts. |
| Trimethylolpropane adduct of xylylene diisocyanate | 0.3 parts. |

COMPARATIVE EXAMPLE 9

By using the pressure-sensitive adhesive solution obtained in the above Example 1, a plaster solution was prepared in such a manner as to give the composition as specified below after drying. Then the procedure of Example 7 was repeated to thereby give a percutaneous absorption preparation. This plaster solution contained no isopropyl myristate.

| | |
|---|---|
| Buprenorphine hydrochloride | 10 parts. |
| Caprylic acid monoglyceride | 45 parts. |
| Pressure-sensitive adhesive (in terms of solid matters) | 44.7 parts. |
| Trimethylolpropane adduct of xylylene diisocyanate | 0.3 parts. |

EXAMPLE 8

A percutaneous absorption preparation was obtained by repeating the procedure of the above Example 4 except for using caproic acid monoglyceride in place of caprylic acid monoglyceride.

EXAMPLE 9

A percutaneous absorption preparation was obtained by repeating the procedure of the above Example 6 except for using buprenorphine in place of buprenorphine hydrochloride.

EXAMPLE 10

Under an inert gas atmosphere, 5 parts of acrylic acid, 75 parts of 2-ethylhexyl acrylate and 20 parts of butyl acrylate were fed into a flask and 0.3 parts of azobisisobutyronitrile was added thereto as a polymerization initiator. Then these monomers were polymerized in ethyl acetate while maintaining the temperature at 60° C. Thus an acrylic pressure-sensitive adhesive solution (solid content: 35%) was obtained.

To 10 parts of buprenorphine were added 30 parts of caproic acid monoglyceride, 10 parts of isopropyl myristate and 210 parts of ethyl acetate. Then, buprenorphine was dissolved by thoroughly stirring. To the resulting dissolution were added 141.86 parts (49.65 parts in terms of solid matters) of the pressure-sensitive adhesive solution described above and 0.35 parts of aluminum diisopropoxide monoethylacetate. After stirring well, a viscous solution was obtained.

This viscous solution was applied onto a polyester releasing liner of 75 μm in thickness in such a manner as to give a dry thickness of 30 μm and dried at 90° C. for 4 minutes. Next, a support, which had been formed by laminating a polyester film of 2 μm in thickness onto a nonwoven polyester fabric (12 $g/m^2$), was adhered thereto. Thus a percutaneous absorption preparation according to the present invention was obtained.

EXAMPLE 11

By using the pressure-sensitive adhesive solution obtained in the above Example 10, a plaster solution was prepared in such a manner as to give the composition as specified below after drying. Then the procedure of Example 10 was repeated to thereby give a percutaneous absorption preparation. This plaster solution contained no aluminum diisopropoxide monoethylacetate.

| | |
|---|---|
| Buprenorphine | 10 parts. |
| Caproic acid monoglyceride | 30 parts. |
| Isopropyl myristate | 10 parts. |
| Pressure-sensitive adhesive (in terms of solid matters) | 50 parts. |

COMPARATIVE EXAMPLE 10

By using the pressure-sensitive adhesive solution obtained in the above Example 10, a plaster solution was prepared in such a manner as to give the composition as specified below after drying. Then the procedure of Example 10 was repeated to thereby give a percutaneous absorption preparation. This plaster solution contained no caproic acid monoglyceride.

| | |
|---|---|
| Buprenorphine | 10 parts. |
| Isopropyl myristate | 10 parts. |
| Pressure-sensitive adhesive (in terms of solid matters) | 79.65 parts. |
| Aluminum diisopropoxide monoethylacetate | 0.35 parts. |

COMPARATIVE EXAMPLE 11

By using the pressure-sensitive adhesive solution obtained in the above Example 10, a plaster solution was prepared in such a manner as to give the composition as specified below after drying. Then the procedure of Example 10 was repeated to thereby give a percutaneous absorption preparation. This plaster solution contained no isopropyl myristate.

| | |
|---|---|
| Buprenorphine | 10 parts. |
| Caproic acid monoglyceride | 30 parts. |
| Pressure-sensitive adhesive (in terms of solid matters) | 59.65 parts. |
| Aluminum diisopropoxide monoethylacetate | 0.35 parts. |

COMPARATIVE EXAMPLE 12

By using the pressure-sensitive adhesive solution obtained in the above Example 10, a plaster solution was prepared in such a manner as to give the composition as specified below after drying. Then the procedure of Example 10 was repeated to thereby give a percutaneous absorption preparation. This plaster solution contained neither caproic acid monoglyceride nor isopropyl myristate.

| | |
|---|---|
| Buprenorphine | 10 parts. |
| Pressure-sensitive adhesive (in terms of solid matters) | 89.65 parts. |
| Aluminum diisopropoxide monoethylacetate | 0.35 parts. |

EXAMPLE 12

To 20 parts of buprenorphine were added 30 parts of caprylic acid monoglyceride, 10 parts of isopropyl myristate and 210 parts of ethyl acetate. Then, buprenorphine was dissolved by thoroughly stirring. To the resulting dissolution were added 113.7 parts (39.8 parts in terms of solid matters) of the pressure-sensitive adhesive solution obtained in Example 9 and 0.2 parts of trimethylolpropane adduct of xylylene diisocyanate. After stirring well, a viscous solution was obtained.

Then the procedure of Example 10 was repeated to thereby give a percutaneous absorption preparation of the present invention having a thickness of 30 μm.

EXAMPLE 13

To 5 parts of buprenorphine hydrochloride were added 30 parts of caprylic acid monoglyceride, 10 parts of isopropyl myristate and 181 parts of ethyl acetate. Then, buprenorphine hydrochloride was dispersed by thoroughly stirring. To the resulting dispersion were added 156.6 parts (54.8 parts in terms of solid matters) of the pressure-sensitive adhesive solution obtained in Example 10 and 0.2 parts of trimethylolpropane adduct of hexamethylene diisocyanate. After stirring well, a viscous solution was obtained.

Then the procedure of Example 10 was repeated to thereby give a percutaneous absorption preparation of the present invention having a thickness of 30 μm.

EXAMPLE 14

To 2.5 parts of buprenorphine hydrochloride and 2.5 parts of buprenorphine, were added 30 parts of caprylic acid monoglyceride, 10 parts of isopropyl myristate and 181 parts of ethyl acetate. Then, buprenorphine hydrochloride was dispersed by thoroughly stirring. To the resulting dispersion were added 156.6 parts (54.8 parts in terms of solid matters) of the pressure-sensitive adhesive solution obtained in Example 10 and 0.2 parts of trimethylolpropane adduct of xylylene diisocyanate. After stirring well, a viscous solution was obtained.

Then the procedure of Example 10 was repeated to thereby give a percutaneous absorption preparation of the present invention having a thickness of 30 μm.

EXAMPLE 15

To 156.6 parts (54.8 parts in terms of solid matters) of the pressure-sensitive adhesive obtained in Example 1 was added 0.08 parts of trimethylolpropane adduct of xylylene diisocyanate. Then the mixture was crosslinked by heating to 65° C. for 2 days. Then the mixture was stirred and dispersed in a homomixer and then mixed with 2.5 parts of buprenorphine hydrochloride, 2.5 parts of buprenorphine, 30 parts of caprylic acid monoglyceride, 10 parts of isopropyl myristate and 181 parts of ethyl acetate. After stirring the mixture well to thereby disperse buprenorphine hydrochloride, a viscous solution was obtained. Then the procedure of Example 10 was repeated. Thus a percutaneous absorption preparation of the present invention having a thickness of 30 μm was obtained.

EXAMPLE 16

Under an inert gas atmosphere, 5 parts of acrylic acid and 95 parts of 2-ethylhexyl acrylate were fed into a flask and 0.3 parts of azobisisobutyronitrile was added thereto as a polymerization initiator. Then these monomers were polymerized in ethyl acetate while maintaining the temperature at 60° C. Thus an acrylic pressure-sensitive adhesive solution (solid content: 40%) was obtained.

To 5 parts of buprenorphine hydrochloride were added 10 parts of caprylic acid monoglyceride, 15 parts of isopropyl myristate, 5 parts of hydrated silicic acid "Carplex #80" (manufactured by Shionogi & Co., Ltd.) and 203 parts of ethyl acetate. Then, buprenorphine hydrochloride and hydrated silicic acid were dispersed by thoroughly stirring the mixture. To the resulting dispersion was added 162.5 parts (65 parts in terms of solid matters) of the pressure-sensitive adhesive solution described above. After stirring well, a viscous solution was obtained.

This viscous solution was applied onto a support, which had been formed by laminating a polyester film of 2 μm in thickness onto a nonwoven polyester fabric (12 g/m$^2$), in such a manner as to give a thickness of 60 μm after drying. After drying at 90° C. for 4 minutes, a polyester releasing liner of 75 μm in thickness was adhered thereto. Thus a percutaneous absorption preparation according to the present invention was obtained.

EXAMPLE 17

To 5 parts of buprenorphine hydrochloride were added 20 parts of caprylic acid monoglyceride, 5 parts of isopropyl myristate, 10 parts of hydrated silicic acid "Carplex #80" (manufactured by Shionogi & Co., Ltd.) and 210 parts of ethyl acetate. Then, buprenorphine hydrochloride and hydrated silicic acid were dispersed by thoroughly stirring the mixture. To the resulting dispersion was added 150 parts (60 parts in terms of solid matters) of the pressure-sensitive adhesive solution obtained in Example 1. After stirring well, a viscous solution was obtained.

Then the procedure of Example 16 was repeated to thereby give a percutaneous absorption preparation of the present invention having a thickness of 60 μm.

EXAMPLE 18

To 5 parts of buprenorphine hydrochloride were added 30 parts of caprylic acid monoglyceride, 10 parts of isopropyl myristate, 10 parts of hydrated silicic acid "Carplex #80" (manufactured by Shionogi & Co., Ltd.) and 233 parts of ethyl acetate. Then, buprenorphine hydrochloride and hydrated silicic acid were dispersed by thoroughly stirring the mixture. To the resulting dispersion Were added 111.75 parts (44.7 parts in terms of solid matters) of the pressure-sensitive adhesive solution obtained in Example 1 and 0.3 parts of trimethylolpropane adduct of hexamethylene diisocyanate. After stirring well, a viscous solution was obtained.

Then the procedure of Example 16 was repeated to thereby give a percutaneous absorption preparation of the present invention having a thickness of 40 μm.

EXAMPLE 19

By using the pressure-sensitive adhesive solution obtained in the above Example 16, a plaster solution was prepared in such a manner as to give the composition as specified below after drying. Then the procedure of Example 18 was repeated to thereby give a percutaneous absorption preparation. This plaster solution contained silicic anhydride "Aerosil A 200" (manufactured by Nippon Aerosil Co., Ltd.) in place of hydrated silicic acid.

| | |
|---|---|
| Buprenorphine hydrochloride | 5 parts. |
| Caprylic acid monoglyceride | 30 parts. |
| Isopropyl myristate | 10 parts. |
| Silicic anhydride ("Aerosil A200") | 10 parts. |
| Trimethylolpropane adduct of hexamethylene diisocyanate | 0.3 parts. |
| Pressure-sensitive adhesive (in terms of solid matters) | 44.7 parts. |

EXAMPLE 20

By using the pressure-sensitive adhesive solution obtained in the above Example 16, a plaster solution was prepared in such a manner as to give the composition as specified below after drying. Then the procedure of Example 18 was repeated to thereby give a percutaneous absorption preparation. This plaster solution contained no silicic anhydride.

| | |
|---|---|
| Buprenorphine hydrochloride | 5 parts. |
| Caprylic acid monoglyceride | 30 parts. |
| Isopropyl myristate | 10 parts. |
| Trimethylolpropane adduct of hexamethylene diisocyanate | 0.3 parts. |
| Pressure-sensitive adhesive (in terms of solid matters) | 54.7 parts. |

COMPARATIVE EXAMPLE 13

By using the pressure-sensitive adhesive solution obtained in the above Example 16, a plaster solution was prepared in such a manner as to give the composition as specified below after drying. Then the procedure of Example 18 was repeated to thereby give a percutaneous absorption preparation. This plaster solution contained no caprylic acid monoglyceride.

| | |
|---|---|
| Buprenorphine hydrochloride | 5 parts. |
| Isopropyl myristate | 10 parts. |
| Hydrated silicic acid ("Carplex #80") | 10 parts. |
| Trimethylolpropane adduct of hexamethylene diisocyanate | 0.3 parts. |
| Pressure-sensitive adhesive (in terms of solid matters) | 74.7 parts. |

COMPARATIVE EXAMPLE 14

By using the pressure-sensitive adhesive solution obtained in the above Example 16, a plaster solution was prepared in such a manner as to give the composition as specified below after drying. Then the procedure of Example 18 was repeated to thereby give a percutaneous absorption preparation. This plaster solution contained no isopropyl myristate.

| | |
|---|---|
| Buprenorphine hydrochloride | 5 parts. |
| Caprylic acid monoglyceride | 30 parts. |
| Hydrated silicic acid ("Carplex #80") | 10 parts. |
| Trimethylolpropane adduct of hexamethylene diisocyanate | 0.3 parts. |
| Pressure-sensitive adhesive (in terms of solid matters) | 54.7 parts. |

COMPARATIVE EXAMPLE 15

By using the pressure-sensitive adhesive solution obtained in the above Example 16, a plaster solution was prepared in such a manner as to give the composition as specified below after drying. Then the procedure of Example 18 was repeated to thereby give a percutaneous absorption preparation. This plaster solution contained neither caprylic acid monoglyceride nor isopropyl myristate.

| | |
|---|---|
| Buprenorphine hydrochloride | 5 parts. |
| Hydrated silicic acid ("Carplex #80") | 10 parts. |
| Trimethylolpropane adduct of hexamethylene diisocyanate | 0.3 parts. |
| Pressure-sensitive adhesive (in terms of solid matters) | 84.7 parts. |

COMPARATIVE EXAMPLE 16

By using the pressure-sensitive adhesive solution obtained in the above Example 16, a plaster solution was prepared in such a manner as to give the composition as specified below after drying. Then the procedure of Example 18 was repeated to thereby give a percutaneous absorption preparation. This plaster solution contained neither caprylic acid monoglyceride, isopropyl myristate nor hydrated silicic acid.

| | |
|---|---|
| Buprenorphine hydrochloride | 5 parts. |
| Trimethylolpropane adduct of hexamethylene diisocyanate | 0.3 parts. |
| Pressure-sensitive adhesive (in terms of solid matters) | 94.7 parts. |

EXAMPLE 21

To 5 parts of buprenorphine hydrochloride were added 30 parts of caprylic acid monoglyceride, 10 parts of isopropyl myristate, 20 parts of hydrated silicic acid "Carplex #80" (manufactured by Shionogi & Co., Ltd.) and 248 parts of ethyl acetate. Then, buprenorphine hydrochloride and hydrated silicic acid were dispersed by thoroughly stirring the mixture. To the resulting dispersion were added 86.75 parts (34.7 parts in terms of solid matters) of the pressure-sensitive adhesive solution obtained in Example 1 and 0.3 parts of trimethylolpropane adduct of hexamethylene diisocyanate. After stirring well, a viscous solution was obtained.

Then the procedure of Example 16 was repeated to thereby give a percutaneous absorption preparation of the present invention having a thickness of 40 μm.

EXAMPLE 22

Under an inert gas atmosphere, 5 parts of acrylic acid, 75 parts of 2-ethylhexyl acrylate and 20 parts of butyl acrylate were fed into a flask and 0.3 parts of azobisisobutyronitrile was added thereto as a polymerization initiator. Then these monomers were polymerized in ethyl acetate while maintaining the temperature at 60° C. Thus an acrylic pressure-sensitive adhesive solution (solid content: 35% was obtained.

To 10 parts of buprenorphine hydrochloride were added 45 parts of caproic acid monoglyceride, 5 parts of isopropyl myristate, 10 parts of hydrated silicic acid "Carplex #80" (manufactured by Shionogi & Co., Ltd.) and 245 parts of ethyl acetate. Then, buprenorphine hydrochloride and hydrated silicic acid were dispersed by thoroughly stirring the mixture. To the resulting dispersion were added 84.6 parts (29.6 parts in terms of solid matters) of the pressure-sensitive adhesive solution described above and 0.4 parts of aluminum diisopropoxide monoethylacetate. After stirring well, a viscous solution was obtained.

This viscous solution was applied onto a polyester releasing liner of 75 μm in thickness in such a manner as to give a dry thickness of 20 μm and dried at 90° C. for 4 minutes. Next, a support, which had been formed by laminating a polyester film of 2 μm in thickness onto a nonwoven polyester fabric (12 g/m²), was adhered thereto. Thus a percutaneous absorption preparation according to the present invention was obtained.

EXAMPLE 23

By using the pressure-sensitive adhesive solution obtained in the above Example 22, a plaster solution was prepared in such a manner as to give the composition as specified below after drying. Then the procedure of Example 22 was repeated to thereby give a percutaneous absorption preparation. This plaster solution contained no hydrated silicic acid.

| | |
|---|---|
| Buprenorphine | 10 parts. |
| Caproic acid monoglyceride | 45 parts. |
| Isopropyl myristate | 5 parts. |
| Aluminum diisopropoxide monoethylacetate | 0.4 parts. |
| Pressure-sensitive adhesive (in terms of solid matters) | 39.6 parts. |

EXAMPLE 24

To 10 parts of buprenorphine were added 20 parts of caprylic acid monoglyceride, 20 parts of isopropyl myristate, 10 parts of hydrated silicic acid "Carplex #80" (manufactured by Shionogi & Co., Ltd.) and 225 parts of ethyl acetate. Then the hydrated silicic acid was dispersed by thoroughly stirring the mixture. To the resulting dispersion were added 113.4 parts (39.7 parts in terms of solid matters) of the pressure-sensitive adhesive solution obtained in Example 22 and 0.3 parts of aluminum diisopropoxide monoethylacetate. After stirring well, a viscous solution was obtained.

This viscous solution was applied onto a polyester releasing liner of 75 μm in thickness in such a manner as to give a dry thickness of 40 μm and dried at 90° C. for 4 minutes. Next, a support, which had been formed by laminating a polyester film of 9 μm in thickness onto an ethylene/vinyl acetate copolymer film of 20 μm in thickness, was adhered thereto. Thus a percutaneous absorption preparation according to the present invention was obtained.

EXAMPLE 25

To 143 parts (49.9 parts in terms of solid matters) of the pressure-sensitive adhesive obtained in Example 22 was added 0.1 parts of trimethylolpropane adduct of hexamethylene diisocyanate. Then the mixture was crosslinked by heating to 60° C. for 2 days. Then the mixture was stirred and dispersed in a homomixer and then mixed with 10 parts of buprenorphine, 20 parts of caproic acid monoglyceride, 10 parts of isopropyl myristate, 10 parts of hydrated silicic acid "Carplex FPS-1" (manufactured by Shionogi & Co., Ltd.) and 307 parts of ethyl acetate. After stirring the mixture well to thereby disperse the hydrated silicic acid, a viscous solution was obtained. Then the procedure of Example 24 was repeated. Thus a percutaneous absorption preparation of the present invention having a thickness of 40 μm was obtained.

TEST EXAMPLE 1

Each of the preparations obtained in the above Examples 1 to 15 and Comparative Examples 1 to 12 was stored at 60° for 2 days and then subjected to the following 9 tests.

(1) Test of Residue on Skin (Adhesive Residue Test)

A preparation was adhered to the inside of a forearm of volunteers (3 for each preparation) for 30 minutes. After peeling off the preparation, it was evaluated whether any residue remained on the adhesion site or not (i.e., the level of adhesive residue). "A" means that no residue was observed; "B" means that a residue was observed exclusively around the edge of the preparation; and "C" means that a residue was observed on some part of the adhesion site or the whole thereof.

(2) Penetration Test on Excised Hairless Rat Skin

Each preparation was adhered to an abdominal skin sample excised from a hairless rat and introduced into a skin penetration test cell of 2-chamber type (effective area: 1.0 cm², volume: 2.5 ml). Then the amount of the drug penetrating through the skin was measured by high performance liquid chromatography and thus the penetration rate was determined. Tables 1 to 4 show the plaster compositions of the preparations and the results of these tests.

TABLE 1

| | Example 1 | Example 2 | Example 3 | Example 4 | Example 5 | Example 6 | Example 7 | Example 8 |
|---|---|---|---|---|---|---|---|---|
| Components | | | | | | | | |
| Buprenorphine Hydrochloride | 5 | 5 | 5 | 5 | 5 | 10 | 10 | 5 |
| Buprenorphine | | | | | | | | |
| Caprylic Acid | 10 | 20 | 20 | 30 | 30 | 35 | 45 | |

TABLE 1-continued

|  | Example 1 | Example 2 | Example 3 | Example 4 | Example 5 | Example 6 | Example 7 | Example 8 |
|---|---|---|---|---|---|---|---|---|
| Monoglyceride Caproic Acid Monoglyceride |  |  |  |  |  |  |  | 30 |
| Isopropyl Myristate | 15 | 10 | 20 | 10 | 10 | 15 | 5 | 10 |
| Adhesive (1) | 69.8 | 64.8 | 54.8 | 54.8 | 55 | 39.7 | 39.7 | 54.8 |
| Adhesive (2) |  |  |  |  |  |  |  |  |
| Crosslinking Agent (1) | 0.2 | 0.2 | 0.2 | 0.2 | — | 0.3 |  | 0.2 |
| Crosslinking Agent (2) |  |  |  |  |  |  | 0.3 |  |
| Crosslinking Agnt (3) |  |  |  |  |  |  |  |  |
| Evaluation |  |  |  |  |  |  |  |  |
| Residue on Skin | A | A | A | A | C | A | A | A |
| Penetration through Excised Skin (Penetration Rate ng/cm$^2$/h) | 3320 | 4140 | 5070 | 7250 | 7310 | 9980 | 6030 | 7610 |

TABLE 2

|  | Example 9 | Example 10 | Example 11 | Example 12 | Example 13 | Example 14 | Example 15 |
|---|---|---|---|---|---|---|---|
| Compnents |  |  |  |  |  |  |  |
| Buprenorphine Hydrochloride |  |  |  |  | 5 | 2.5 | 2.5 |
| Buprenorphine | 10 | 10 | 10 | 20 |  | 2.5 | 2.5 |
| Caprylic Acid Monoglyceride | 35 |  |  | 30 | 30 | 30 | 30 |
| Caproic Acid Monoglyceride |  | 30 | 30 |  |  |  |  |
| Isopropyl Myristate | 15 | 10 | 10 | 10 | 10 | 10 | 10 |
| Adhesive (1) | 39.7 |  |  |  |  |  | 54.8 |
| Adhesive (2) |  | 49.65 | 50 | 39.8 | 54.8 | 54.8 |  |
| Crosslinking Agent (1) | 0.3 |  |  |  | 0.2 |  |  |
| Crosslinking Agent (2) |  |  |  | 0.2 |  | 0.2 | 0.08 |
| Crosslinking Agent (3) |  | 0.35 | — |  |  |  |  |
| Evaluation |  |  |  |  |  |  |  |
| Residue on Skin | A | A | C | A | A | A | A |
| Penetration through Excised Skin (Penetration Rate ng/cm$^2$/h) | 9840 | 7990 | 8010 | 12140 | 5030 | 4990 | 5010 |

TABLE 3

|  | Comp. Example 1 | Comp. Example 2 | Comp. Example 3 | Comp. Example 4 | Comp. Example 5 | Comp. Example 6 |
|---|---|---|---|---|---|---|
| Components |  |  |  |  |  |  |
| Buprenorphine Hydrochloride |  |  |  |  |  |  |
| Buprenorphine | 5 | 5 | 5 | 5 | 5 | 5 |
| Caprylic Acid Monoglyceride | 10 | 10 | — | 30 | — | — |
| Caproic Acid Monoglyceride |  |  |  |  |  |  |
| Isopropyl Myristate | — | 5 | 10 | — | — | — |
| Adhesive (1) | 84.8 | 79.8 | 84.8 | 64.8 | 94.8 | 95 |

TABLE 3-continued

|  | Comp. Example 1 | Comp. Example 2 | Comp. Example 3 | Comp. Example 4 | Comp. Example 5 | Comp. Example 6 |
|---|---|---|---|---|---|---|
| Adhesive (2) |  |  |  |  |  |  |
| Crosslinking Agent (1) | 0.2 | 0.2 | 0.2 | 0.2 | 0.2 | — |
| Crosslinking Agent (2) |  |  |  |  |  |  |
| Crosslinking Agent (3) |  |  |  |  |  |  |
| Evaluation |  |  |  |  |  |  |
| Residue on Skin | A | A | A | A | A | A |
| Penetration through Excised Skin (Penetration Rate ng/cm²/h) | 590 | 1420 | 37 | 2250 | 25 | 27 |

TABLE 4

|  | Comp. Example 7 | Comp. Example 8 | Comp. Example 9 | Comp. Example 10 | Comp. Example 11 | Comp. Example 12 |
|---|---|---|---|---|---|---|
| Components |  |  |  |  |  |  |
| Buprenorphine Hydrochloride | 10 | 10 | 10 |  |  |  |
| Buprenorphine |  |  |  | 10 | 10 | 10 |
| Caprylic Acid Monoglyceride | — | — | 45 |  |  |  |
| Caproic Acid Monoglyceride |  |  |  | — | 30 | — |
| Isopropyl Myristate | — | 5 | — | 10 | — | — |
| Adhesive (1) | 89.7 | 84.7 | 44.7 |  |  |  |
| Adhesive (2) |  |  |  | 79.65 | 59.65 | 89.65 |
| Crosslinking Agent (1) | 0.3 |  |  |  |  |  |
| Crosslinking Agent (2) |  | 0.3 | 0.3 |  |  |  |
| Crosslinking Agent (3) |  |  |  | 0.35 | 0.35 | 0.35 |
| Evaluation |  |  |  |  |  |  |
| Residue on Skin | A | A | A | A | A | A |
| Penetration through Excised Skin (Penetration Rate ng/cm²/h) | 37 | 28 | 2980 | 42 | 2340 | 32 |

Adhesive (1): acrylic acid: 2-ethylhexyl acrylate=5:95.
Adhesive (2): acrylic acid: 2-ethylhexyl acrylate: butyl acrylate=5:75:20.
Crosslinking Agent (1): trimethylolpropane adduct of hexamethylene diisocyanate.
Crosslinking Agent (2): trimethylolpropane adduct of xylylene diisocyanate.
Crosslinking Agent (3): aluminum diisopropoxide monoethylacetate.

The percutaneous absorption preparations of the present invention each showed high skin penetration of buprenorphine (hydrochloride).

A comparison between the result of Example 1 with the results of Comparative Examples of 1 and 2 indicates the following facts. The preparation containing caprylic acid monoglyceride alone as a penetration enhancer showed poor skin penetration (Comparative Example 1). Although caprylic acid monoglyceride was used together with isopropyl myristate, a sufficient skin penetration rate could not be achieved when the total amount of the penetration enhancer was 15% by weight (Comparative Example 2). In contrast thereto, the preparation, which contained caprylic acid monoglyceride together with isopropyl myristate and the penetration enhancer in a total amount of 25% by weight, showed remarkably improved skin penetration (Example 1).

A comparison between the results of Examples 4 and 5 with the results of Comparative Examples of 3 to 6 indicates the following facts. The preparations containinig caprylic acid monoglyceride together with isopropyl myristate (Examples 4 and 5) showed synergistically elevated skin penetration rates, compared with the preparations containing either of these components alone (Comparative Examples 3 and 4). The crosslinked preparation (Example 4) resulted in no adhesive residue (cohesive failure).

A comparison between the result of Example 7 with the results of Comparative Examples of 8 and 9 indicates the following fact. The preparation containing caprylic acid monoglyceride together with isopropyl myristate (Example 7) showed a synergistically elevated skin penetration rate, compared with the preparations containing either of these components alone (Comparative Examples 8 and 9).

A comparison between the results of Examples 10 and 11 with the results of Comparative Examples of 10 to 12 indicates the following facts. The preparations containing caproic acid monoglyceride together with isopropyl myristate (Examples 10 and 11) showed synergistically elevated skin penetration rates, compared with the preparations containing either of these components alone (Comparative Examples 10 and 11). The crosslinked preparation (Example 10) resulted in no adhesive residue (cohesive failure).

(3) Adhesion Test on Beagle (Determination of Blood Level of Drug)

The chest-abdominal part of a beagle was carefully shaved with a shaver and the preparations of Example 6 and Comparative Example 7 were adhered thereto in a dose of 3 $cm^2$/kg. Then the blood level was monitored by gas chromatography with the passage of time. Table 5 shows the results.

TABLE 5

| | Blood Level (ng/ml) | |
|---|---|---|
| Time (hrs) | Example 6 | Comparative Example 7 |
| 0.5 | 0.44 | ≦ detection limit (0.05 ng/ml) |
| 1 | 0.74 | ≦ detection limit (0.05 ng/ml) |
| 2 | 1.56 | ≦ detection limit (0.05 ng/ml) |
| 4 | 2.68 | ≦ detection limit (0.05 ng/ml) |
| 8 | 3.01 | ≦ detection limit (0.05 ng/ml) |
| 12 | 2.99 | ≦ detection limit (0.05 ng/ml) |
| 16 | 2.80 | ≦ detection limit (0.05 ng/ml) |
| 20 | 2.70 | ≦ detection limit (0.05 ng/ml) |
| 24 | 2.68 | ≦ detection limit (0.05 ng/ml) |

The percutaneous absorption preparation according to the present invention could sustain a high blood level in a stable state over a long period of time.

TEST EXAMPLE 2

Each of the preparations obtained in the above Examples to 16 to 25 and Comparative Examples 13 to 16 was stored at 60° C. for 2 days and then subjected to the following tests.

(1) Test of Residue on Skin (Adhesive Residue Test)

A preparation was adhered to the inside of a forearm of volunteers (3 for each preparation) for 30 minutes. After peeling off the preparation, it was evaluated whether any residue remained on the adhesion site or not (i.e., the level of adhesive residue). "A" means that no residue was observed; "B" means that a residue was observed exclusively around the edge of the preparation; and "C" means that a residue was observed on some part of the adhesion site or the whole thereof.

(2) Penetration Test on Excised Hairless Rat Skin

Each preparation Was adhered to an abdominal skin sample excised from a hairless rat and introduced into a skin penetration test cell of 2-chamber type (effective area: 1.0 $cm^2$, volume: 2.5 ml). Then the amount of the drug penetrating through the skin was measured by high performance liquid chromatography and thus the penetration rate was determined. Tables 6 and 7 show the plaster compositions of the preparations and the results of these tests.

TABLE 6

| | Example 16 | Example 17 | Example 18 | Example 19 | Example 20 | Example 21 | Example 22 | Example 23 | Example 24 | Example 25 |
|---|---|---|---|---|---|---|---|---|---|---|
| Components | | | | | | | | | | |
| Buprenorphine hydrochloride | 5 | 5 | 5 | 5 | 5 | 5 | 10 | | | |
| Buprenorphine | | | | | | | | 10 | 10 | 10 |
| Caprylic Acid Monoglyceride | 10 | 20 | 30 | 30 | 30 | 30 | | | 20 | |
| Caproic Acid Monoglyceride | | | | | | | 45 | 45 | | 20 |
| Isopropyl Myristate | 15 | 5 | 10 | 10 | 10 | 10 | 5 | 5 | 20 | 10 |
| Hydrated Silicic Acid (#80) | 5 | 10 | 10 | — | 20 | 10 | — | 10 | | |
| Hydrated Silicic Acid (FPS-1) | | | | | | | | | | 10 |
| Silicic an-Hydride (A200) | | | | 10 | | | | | | |
| Adhesive (1) | 65 | 60 | 44.7 | 44.7 | 54.7 | 34.7 | | | | |
| Adhesive (2) | | | | | | | 29.6 | 39.6 | 39.7 | 49.9 |
| Crosslinking Agent (1) | | | 0.3 | 0.3 | 0.3 | 0.3 | | | | 0.1 |
| Crosslinking Agent (2) | | | | | | | 0.4 | 0.4 | 0.3 | |
| Crosslinking | | | | | | | | | | |

TABLE 6-continued

| | Example 16 | Example 17 | Example 18 | Example 19 | Example 20 | Example 21 | Example 22 | Example 23 | Example 24 | Example 25 |
|---|---|---|---|---|---|---|---|---|---|---|
| Agent (3) | | | | | | | | | | |
| Evaluation | | | | | | | | | | |
| Residue on Skin | A | A | A | A | A | A | A | A | A | A |
| Penetration through Excised Skin (Penetration Rate ng/cm²/h) | 3270 | 3960 | 4820 | 4770 | 4930 | 4940 | 6150 | 6190 | 5070 | 3910 |

TABLE 7

| | Comp. Example 13 | Comp. Example 14 | Comp. Example 15 | Comp. Example 16 |
|---|---|---|---|---|
| Components | | | | |
| Buprenorphine Hydrochloride | 5 | 5 | 5 | 5 |
| Buprenorphine | | | | |
| Caprylic Acid Monoglyceride | — | 30 | — | — |
| Caproic Acid Monoglyceride | | | | |
| Isopropyl Myristate | 10 | — | — | — |
| Hydrated Silicic Acid (#80) | 10 | 10 | 10 | — |
| Hydrated Silicic Acid (FPS-1) | | | | |
| Silicic anHydride (A200) | | | | |
| Adhesive (1) | 74.7 | 54.7 | 84.7 | 94.7 |
| Adhesive (2) | | | | |
| Crosslinking Agent (1) | 0.3 | 0.3 | 0.3 | 0.3 |
| Crosslinking Agent (2) | | | | |
| Crosslinking Agent (3) | | | | |
| Evaluation | | | | |
| Residue on Skin | A | A | A | A |
| Penetration through Excised Skin (Penetration Rate ng/cm²/h) | 30 | 1620 | 20 | 22 |

Adhesives (1) and (2) and Corsslinking Agents (1) to (3) given in the above tables are those as defined above.

Hydrated Silicic Acid (#80): "Carplex #80" (manufactured by Shionogi & Co., Ltd.).

Hydrated Silicic Acid (FPS-1): "Carplex FPS-1" (manufactured by Shionogi & Co., Ltd.).

Silicic Anhydride (A200): "Aerosil A200" (manufactured by Nippon Aerosil Co., Ltd.).

The percutaneous absorption preparations of the present invention each showed high skin penetration of buprenorphine (hydrochloride).

A comparison between the result of Example 18 with the results of Comparative Examples of 13 to 16 indicates the following fact. The preparations containing caprylic acid monoglyceride together with isopropyl myristate (Example 18) showed a synergistically elevated skin penetration rate, compared with the preparations containing either of these components alone (Comparative Examples 13 and 14).

(3) Adhesion Test on Beagle (Determination of Blood Level)

The chest-abdominal part of a beagle was carefully shaved with a shaver and the preparations of Example 18 and Comparative Example 16 were adhered thereto in a dose of 3 cm²/kg. Then the blood level was monitored by gas chromatography-mass spectrometry with the passage of time. Table 8 shows the results.

TABLE 8

| | Blood Level (ng/ml) | |
|---|---|---|
| Time (hrs) | Example 18 | Comparative Example 16 |
| 0.5 | 0.30 | ≦ detection limit (0.05 ng/ml) |
| 1 | 0.51 | ≦ detection limit (0.05 ng/ml) |
| 2 | 1.01 | ≦ detection limit (0.05 ng/ml) |
| 4 | 1.76 | ≦ detection limit (0.05 ng/ml) |
| 8 | 1.99 | ≦ detection limit (0.05 ng/ml) |
| 12 | 2.02 | ≦ detection limit (0.05 ng/ml) |
| 16 | 1.93 | ≦ detection limit (0.05 ng/ml) |
| 20 | 1.89 | ≦ detection limit (0.05 ng/ml) |
| 24 | 1.88 | ≦ detection limit (0.05 ng/ml) |

The percutaneous absorption preparation according to the present invention could sustain a high blood level in a stable state over a long period of time.

(4) Drug Elution Test

This test was performed with the use of the preparations of Examples 18, 19, 20, 22 and 23. 20 cm² of each preparation was soaked in 800 ml of water at 32° C. and stirred at a paddle rotational speed of 100 rpm. Then the test solution was sampled with the passage of time and the content of the drug in each sample was determined by liquid chromatography. From the obtained data, the amount of the drug eluted from the preparation was determined and the elution ratio ((the amount eluted/the amount contained in the preparation prior to the test)×100 (%)) was calculated based on the drug content of the preparation prior to the test. Also, the preparations were stored at 60° C. for 2 months and then subjected to the same test. Table 9 summarizes the results.

TABLE 9

| | Storage Time | Elution Ratio (%) | | | |
|---|---|---|---|---|---|
| Example No. | (months) | 0.5 hr | 1 hr | 2 hrs | 4 hrs |
| Example 18 | 0 | 22 | 36 | 57 | 80 |
| | 2 | 24 | 39 | 60 | 84 |

TABLE 9-continued

| Example No. | Storage Time (months) | Elution Ratio (%) | | | |
|---|---|---|---|---|---|
| | | 0.5 hr | 1 hr | 2 hrs | 4 hrs |
| Example 19 | 0 | 72 | 80 | 84 | 90 |
| | 2 | 22 | 26 | 31 | 43 |
| Example 20 | 0 | 16 | 21 | 29 | 40 |
| | 2 | 23 | 33 | 51 | 72 |
| Example 22 | 0 | 59 | 78 | 93 | 96 |
| | 2 | 63 | 84 | 95 | 98 |
| Example 23 | 0 | 25 | 38 | 49 | 63 |
| | 2 | 35 | 52 | 71 | 92 |

The preparations of Examples 18 and 22 containing hydrated silicic acid showed little changes in the elution ratio after storing at 60° C. for 2 months. In contrast, the preparations of Examples 20 and 23 containing no hydrated silicic acid showed large changes in the elution ratio, while the preparation of Example 19 containing silicic anhydride showed a large decrease in the elution ratio.

Because of containing a monoglyceride of a fatty acid having 6 to 8 carbon atoms and isopropyl myristate as a penetration enhancer, the percutaneous absorption preparation of the present invention has synergistically elevated skin penetration of buprenorphine (hydrochloride) and can sustain a high blood level in a stable state over a long period of time.

In the case of the percutaneous absorption preparation of the present invention containing hydrated silicic acid in the plaster, the oozing out of the penetration enhancer during the storage is prevented and the preparation suffers from little changes in the properties (elution of the drug, etc.) and has a high storage stability. This preparation has additional advantages such that the plaster solution can be easily applied and the formation of a plaster layer can be facilitated.

Furthermore, a preparation containing a crosslinked pressure-sensitive adhesive is excellent in skin penetration and shape retention. It also results in no residue on the skin (adhesive residue) after peeling off. These characteristics make it highly suitable for practical use.

The percutaneous absorption preparation of the present invention, by which a non-narcotic analgesic buprenorphine can be percutaneously administered in an effective dose continuously, is useful in relieving cancerous pain and postoperative pain.

While the invention has been described in detail with reference to specific embodiments, it will be apparent to one skilled in the art that various changes and modifications can be made to the invention without departing from its spirit and scope.

What is claimed is:

1. A percutaneous absorption preparation for administering buprenorphine hydrochloride and/or buprenorphine, which comprises a support having on one surface thereof a plaster layer containing a pressure-sensitive adhesive, buprenorphine hydrochloride and/or buprenorphine, and a penetration enhancer, wherein the penetration enhancer consists essentially of a combination of a monoglyceride of fatty acid having 6 to 8 carbon atoms and isopropyl myristate, and the plaster layer contains at least 10% by weight of a monoglyceride of a fatty acid having 6 to 8 carbon atoms and at least 5% by weight of isopropyl myristate, with the proviso that the content of the whole penetration enhancer ranges from 25 to 50 by weight.

2. The percutaneous absorption preparation of claim 1, wherein the pressure-sensitive adhesive is a copolymer of acrylic acid with an acrylic monomer copolymerizable with acrylic acid, which has a pressure-sensitive adhesive property.

3. The percutaneous absorption preparation of claim 2, wherein the pressure-sensitive adhesive is a copolymer of acrylic acid with an alkyl acrylate having from 4 to 15 carbon atoms in the alkyl group.

4. The percutaneous absorption preparation of claim 3, wherein the pressure-sensitive adhesive is a copolymer of acrylic acid with 2-ethylhexyl acrylate.

5. The percutaneous absorption preparation of claim 1, which the plaster layer further contains from 2.5 to 20% by weight of hydrated silicic acid.

6. The percutaneous absorption preparation of claim 1, wherein the pressure-sensitive adhesive is crosslinked.

7. The percutaneous absorption preparation of claim 1, wherein the plaster layer contains from 2.5 to 20% by weight of buprenorphine hydrochloride and/or buprenorphine.

* * * * *